United States Patent [19]
Abramshe et al.

[11] Patent Number: 6,165,952
[45] Date of Patent: Dec. 26, 2000

[54] ASHLESS RUST INHIBITOR LUBRICANT COMPOSITIONS

[75] Inventors: Richard A. Abramshe, Highland, N.Y.; Werner J. Blank, Wilton; Edward T. Hessell, Fairfield, both of Conn.

[73] Assignee: King Industries, Inc., Norwalk, Conn.

[21] Appl. No.: 09/286,560

[22] Filed: Apr. 5, 1999

[51] Int. Cl.[7] .................. C10M 129/76; C10M 145/22; C10M 149/18
[52] U.S. Cl. .................... 508/477; 560/155; 560/179
[58] Field of Search .................. 508/477; 560/155, 560/179

[56] References Cited

U.S. PATENT DOCUMENTS

| | | | |
|---|---|---|---|
| Re. 34,459 | 11/1993 | Bullen et al. | 252/51.5 |
| 3,341,573 | 9/1967 | Shibe | 508/477 |
| 3,679,585 | 7/1972 | Brook et al. | 252/51.5 |
| 3,703,587 | 11/1972 | Spanos, III et al. | 21/2.5 |
| 3,964,954 | 6/1976 | Morduchowitz | 156/331 |
| 3,996,144 | 12/1976 | Weetman et al. | 252/56 |
| 4,165,292 | 8/1979 | Davis et al. | 252/51.5 |
| 4,170,560 | 10/1979 | Lowe | 252/47.5 |
| 4,177,041 | 12/1979 | Sung et al. | 44/71 |
| 4,199,462 | 4/1980 | Soula et al. | 252/51.5 |
| 4,203,730 | 5/1980 | Hanson | 44/71 |
| 4,228,282 | 10/1980 | Hotten | 544/296 |
| 4,233,176 | 11/1980 | Conner, Sr. | 252/392 |
| 4,253,876 | 3/1981 | Godar et al. | 106/14.42 |
| 4,326,987 | 4/1982 | Hendricks et al. | 252/392 |
| 4,409,411 | 10/1983 | Pez | 585/275 |
| 4,448,974 | 5/1984 | O'Brien et al. | 548/550 |
| 4,462,918 | 7/1984 | Matthews et al. | 252/32.7 |
| 4,647,390 | 3/1987 | Buckley, III et al. | 252/51.5 |
| 4,743,388 | 5/1988 | Lege | 252/51.5 |
| 4,749,500 | 6/1988 | Forsberg et al. | 252/49.3 |
| 4,798,612 | 1/1989 | Plavac et al. | 44/63 |
| 4,892,671 | 1/1990 | O'Neil et al. | 252/51.5 |
| 4,920,058 | 4/1990 | DeBlase et al. | 436/85 |
| 4,957,641 | 9/1990 | Borggrefe et al. | 252/34 |
| 5,055,230 | 10/1991 | Clubley et al. | 252/389 |
| 5,069,684 | 12/1991 | Blain et al. | 44/331 |
| 5,254,277 | 10/1993 | Gentit et al. | 252/51.5 |
| 5,275,749 | 1/1994 | Kugel et al. | 252/51.5 |
| 5,312,555 | 5/1994 | Malfer | 252/51.5 |
| 5,486,301 | 1/1996 | Abramo et al. | 252/51.5 |

FOREIGN PATENT DOCUMENTS 0086513  8/1983  European Pat. Off. ..... C10M 141/06

*Primary Examiner*—Margaret Medley
*Assistant Examiner*—Cephia D. Toomer
*Attorney, Agent, or Firm*—Hedman, Gibson & Costigan, P.C.

[57] ABSTRACT

A unique ashless composition of matter, a method for its preparation and its use as an improved corrosion inhibitor additive for formulated industrial lubricants is disclosed.

31 Claims, No Drawings

ASHLESS RUST INHIBITOR LUBRICANT COMPOSITIONS

The present invention relates to corrosion inhibitors. More particularly, the present invention concerns corrosion inhibitors for use with lubricants, a process for making the inhibitors and lubricants prepared therefrom.

BACKGROUND OF THE INVENTION

Modern formulated industrial oils typically use corrosion inhibitors to prevent the formation of rust on steel parts. It is well known that certain types of carboxylic acids act as corrosion inhibitors. In particular, alkylated succinic acids and their mono ester derivatives are well known in the art as corrosion inhibitors for hydraulic fluids and gear oils.

For example, U.S. Pat. No. 4,409,411 describes the reaction product of an alkyl substituted succinic anhydride and a polyol as a corrosion inhibitor for fuels and lubricants. U.S. Pat. No. 4,165,292 describes a mixture of a basic amine compound with a succinic acid derivative as a corrosion inhibitor for lubricants.

In addition, several acylated aspartic acid derivatives, such as those described in U.S. Pat. Nos. 5,275,749 and 4,462,918 and European Patent No. 86 513 are known in the art.

It is also known in the art to employ compounds possessing both carboxylic acid and hydroxyl functional groups as corrosion inhibitors for a variety of applications. For example, U.S. Pat. No. 5,055,230 discloses the use of a composition containing hydroxy, ether and carboxylic acid functionality as a corrosion inhibitor for aqueous and oil based systems. U.S. Pat. No. 4,892,671 describes aminoethyl-2-propanol derivatives as corrosion inhibitors for ferrous metal. U.S. Pat. No. 5,254,277 discloses a combination of bis(hydroxyethyl)tallow amine and an alkyltallowdiamine dicarboxylate as a corrosion inhibitor for polyol ester fluids. U.S. Pat. No. 4,957,641 describes alkyloxyhydroxy fatty acids and salts thereof as useful corrosion inhibitors in oils and oil-containing emulsions. U.S. Pat. No. 4,233,176 discloses a solution consisting of monobasic acids, a lubricant, a mixture of amines, and water as a corrosion inhibitor system for metals prior to painting. U.S. Pat. No. 4,743,388 teaches a complex amide carboxylate anti-corrosion additive for metal working fluids.

Formulated hydraulic fluids, gear oils, and circulating oils typically use mineral oil base stocks as the major lubricating component. These base oils are used in conjunction with various additives such as antioxidants, antiwear agents, and corrosion inhibitors to obtain a final formulation which meets the performance requirements of the particular industrial oil application.

In recent years there have been several major advances in the refining of mineral base oils. Process steps such as severe hydrotreating remove any unsaturation and impurities from the oils. The result is a base oil with improved thermal stability. In addition, there is now increased use of non-polar synthetic base oils such as poly-alphaolefins as base oils for formulated lubricants.

As the performance of hydraulic oils, gear oils and other industrial oils become more severe, industrial lubricant formulators have begun to use severely hydrotreated base oils and synthetic base oils such as poly-alpha-olefins because of their low cost and their improved thermal stability relative to conventional mineral oil base stocks. However, there are certain disadvantages to the use of these highly refined base oils. Most of the commonly used lubricant additives such as amine antioxidants, phenolic antioxidants, antiwear additives and corrosion inhibitors have decreased solubility in hydrotreated base stocks and/or poly-alpha-olefins. More importantly, such changes in additive solubility in many cases negatively effects the performance of the additives (heretoafter referred to as additive response). In general, the additive response decreases significantly in the highly refined base oils or non-polar synthetic base oils. This phenomenon may be more pronounced for those additives which function as surface active agents.

It has unexpectedly been discovered that the ashless compositions of matter of the present invention have excellent solubility in severely hydrotreated base oils and non-polar synthetic base oils such as poly-alpha-olefins as well as traditional mineral oils and, when incorporated in relatively small amounts, dramatically improve the rust protection properties of finished hydraulic fluids formulated with highly paraffinic and severely hydrotreated mineral base oils, or non-polar synthetic base oils such as poly-alpha-olefins.

SUMMARY OF THE PRESENT INVENTION

To this end the present invention provides an improved ashless (all organic) composition of matter which has application as a corrosion inhibitor.

It is therefore an object of the present invention to provide a composition of matter which has application as a corrosion inhibitor for use with lubricants.

It is a further object of the present invention to provide a corrosion inhibitor composition having improved solubility in severely hydrotreated base oils and non-polar synthetic base oils such as polyalphaolefins.

It is a further object of the present invention to provide an improved lubricant composition.

It is another further object of the present invention to provide a lubricant composition which comprises a small proportion of an ashless composition of matter and a major proportion of a hydrocarbon of lubricating viscosity which prevents or substantially reduces the formation of rust on steel. The lubricating compositions may further comprise conventional additives selected from the group consisting of antiwear additives, antioxidants, yellow metal deactivators, viscosity index improvers, extreme pressure agents and mixtures of any of the foregoing.

It is a still further object of the present invention to employ the ashless corrosion inhibitor of the present invention in other applications such as, but not limited to, coatings, paints, temporary rust preventatives and adhesives.

DETAILED DESCRIPTION OF THE PRESENT INVENTION

The present invention provides a unique ashless composition of matter that has been found to be an excellent corrosion inhibitor additive for formulated industrial lubricants. The lubricating compositions of the present invention will generally comprise from about 0.01 to about 10.0 percent by weight of the corrosion inhibitor additive of the present invention, preferably from about 0.01 to about 5.0 percent by weight, more preferably from about 0.01 to about 0.1 percent by weight. In most instance the use of less than about 0.1 percent by weight of the corrosion inhibitor additive of the present invention will provide a lubricant composition which possesses excellent rust preventitive characteristics on steel.

The corrosion inhibitor additives of the present invention are those of the general formula

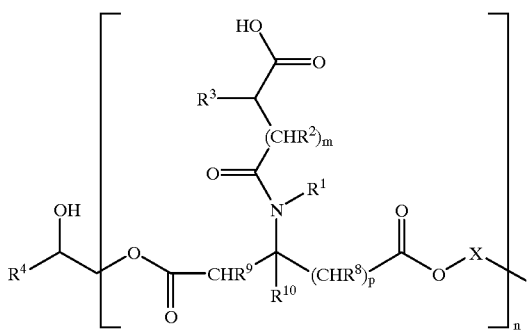

(I)

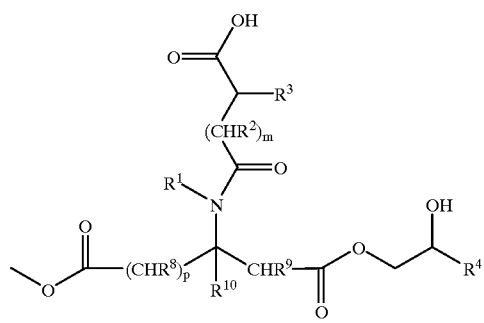

wherein n is an integer from 0 to about 5, m is an integer of from 1 to about 6, p is an integer of from 0 to about 6 or more, each X independently comprises the same or different saturated or unsaturated, branched or linear hydrocarbon diradical having from about 3 to about 8 carbon atoms, or an alkylene glycol or polyglycol of the general structure

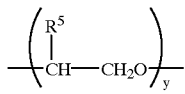

where each R is independently the same or different saturated alkyl group of from 1 to about 4 carbon atoms or H and y is an integer of from 1 to about 20; each R' may comprise the same or different branched or linear, saturated or unsaturated hydrocarbon group of from about 6 to about 30 carbon atoms or an alkyloxypropyl group wherein the alkyl group is a branched or linear saturated hydrcarbon group of from about 1 to about 18 carbon atoms in length; $R^2$ and $R^3$ are independently the same or different saturated or mono-unsaturated linear or branched hydrocarbon group of from about 12 to about 30 carbon atoms or H; each $R^4$ may independently comprise the same or different linear or branched saturated hydrocarbon group of from about 6 to about 22 carbon atoms, or a moiety of the general formula:

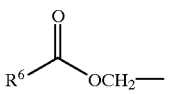

where R is a saturated branched or linear hydrocarbon group of from about 6 to about 20 carbon atoms, or a moiety of the general formula:

where $R^7$ is a hydrocarbon group of from about 1 to about 10 carbon atoms; and each $R^8$, $R^9$ and $R^{10}$ independently comprise the same or different saturated or unsaturated, branched or linear, hydrocarbon radicals having from 1 to about 20 carbon atoms or H.

The additives of the present invention are prepared by a novel process comprising reacting (a) a diol, (b) an unsaturated diacid or corresponding anhydride, (c) an epoxide, (d) a primary amine, and (e) an anhydride which is the same or different from the anhydride of reactant (b) in a manner to prepare the compositions of the present invention as more fully discussed hereinbelow.

The additives are particularly effective as rust inhibitors in highly non-polar base oils such as poly-alpha-olefins, or hydrotreated paraffinic base oils where certain other rust inhibitors commonly known to those skilled in the art of lubrication and tribology are not effective. The use of the term "hydrotreated base oils" as used throughout the present specification is meant to describe those base oils which, during refining and manufacture, are subjected to a hydrogenation process which removes most or all of the unsaturation in the hydrocarbon. The process is commonly referred to by those of ordinary skill in the art as severe hydrotreating. Such base oils are commonly referred to as Group II or Group III base oils by those skilled in the art of industrial lubricant formulation.

Although the present invention is described in terms of improving the rust preventitive characteristics of lubricants, the present invention is also intended to cover the many other applications in which the additive compositions of the present invention may be employed, such as, but not limited to, coatings, paints, adhesives and other industrial products.

The additive compositions according to formula I above of the present invention may be prepared by combining the various reagents in a stepwise fashion, such as by a process comprising (a) reacting an unsaturated dicarboxylic acid or its corresponding anhydride with a diol, an epoxide or a combination thereof to form a first intermediate unsaturated polyester having terminal beta-hydroxyalkylester groups, (b) reacting said first intermediate unsaturated polyester with a primary amine to form a second intermediate amine functional polyester, and (c) reacting said second intermediate with an anhydride which is the same as or different from the anhydride of step (a) to provide an acylated amine functional polyester containing terminal beta-hydroxy ester groups product. In the first step a diol (reactant A) and a diacid or corresponding anhydride having an activated double bond (reactant B) are reacted in a condensation reaction to give a first intermediate of general structure II as set forth in equation (1) below.

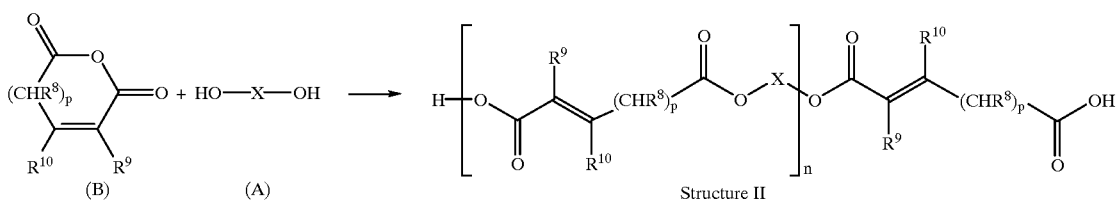

(1)

Preferably the reaction is conducted using standard techniques and conditions for ester synthesis from an alcohol and an acid as are known to those of ordinary skill in the art. The reaction is typically carried out using a small portion of an amine catalyst as is known to those skilled in the art, but is not necessary. The molar ratio of reactant A to reactant B may be in the range of from about 0:1 to about 1:3, and is typically in the range from about 1:1 to about 1:3, but is preferably about 1:2.

Reactant A is a diol having the general formula:

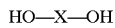

wherein X may comprise (i) a saturated or unsaturated branched or linear, hydrocarbon diradical having from about 3 to about 8 carbon atoms, or (ii) an alkylene glycol or polyglycol of the general structure:

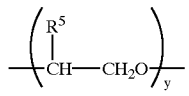

wherein each $R^5$ is independently the same or different saturated alkyl group of from 1 to about 4 carbon atoms or H and y is an integer of from 1 to about 20.

Practically any of these diols known to those of ordinary skill in the art may be employed as reactant A in the first step of the preparation, but preferred diols for use as reactant A of the present invention are branched or linear saturated hydrocarbon diols such as, but not limited to: neopentyl glycol, ethylene glycol, propylene glycol, 1,4-butanediol, methylpentanediol and 1,6-hexanediol and mixtures of any of the foregoing. The diols useful as reactant A in the practice of the present invention may also contain other heteroatoms such as nitrogen, sulfur or oxygen. Therefore, diols such as polyetherdiols or sulfide diols are also useful in the practice of the present invention. Non-limiting examples of such diols are: ethylene diglycol, dipropylene glycol, polyethylene glycols, polypropylene glycols, mixed polypropylene/ethylene glycols, 2,2'-thiodiethanol and methyldiethanolamine and mixtures of any of the foregoing.

In a preferred embodiment reactant B is maleic anhydride, however, any imaginable diacid or its corresponding anhydride known to those skilled in the art containing an activated double bond may be employed. The term "activated double bond" refers to those double bonds which are capable of undergoing reaction with an N—H moiety. Most common are those double bonds which are in conjugation with an electron withdrawing group such as a carbonyl group (C=O) which polarizes the double bond toward addition of nucleophiles. The anhydrides (and corresponding diacids) useful in the practice of the present invention as reactant B will generally be of the formula:

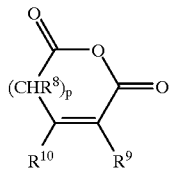

wherein p is an integer ranging from 0 to about 6 and $R^8$, $R^9$ and $R^{10}$ are independently a saturated or unsaturated, branched or linear, hydrocarbon radical having from about 1 to about 20 carbon atoms or H. Therefore, maleic acid, maleic anhydride, itaconic acid, itaconic anhydride and mixtures of any of the foregoing are examples of materials suitable for use as reactant B. Reaction of the diol with the anhydride (or diacid) results in a monoacid ester, the acid group of which may undergo further reaction with more diol.

In the second step, the intermediate of general structure II is reacted with a suitable portion of an epoxide (reactant C) to react with at least a portion of, most of, or all of, the carboxylic acid groups, as generally shown in Equation (2) below to produce a second intermediate of general formula III.

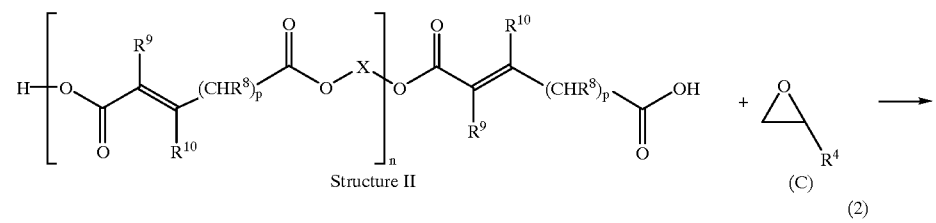

(2)

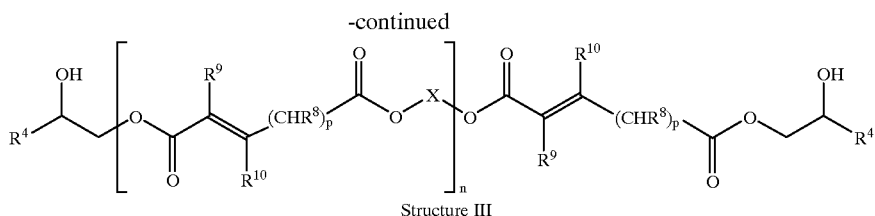

Structure III

The epoxide reaction can be carried out at a temperature of from about 100° C. to about 170° C. but is typically conducted at a temperature of about 150° C. for from about 5 to about 6 hours. The reaction is heated until the acid number of the reaction is less than about 15 mg KOH/g (the acid number is defined as the amount of potassium hydroxide, in mg, that is required to neutralize 1.0 gram of a material).

Suitable epoxides useful as reactant C in the practice of the present invention have the general formula:

wherein R comprises (i) a linear or branched saturated hydrocarbon group of from about 6 carbon atoms to about 22 carbon atoms, or (ii) a moiety of the general structure

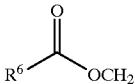

where $R^6$ is a saturated branched or linear hydrocarbon group of from about 6 to about 20 carbon atoms, or (iii) a moiety of the general structure

wherein $R^7$ is a hydrocarbon group of from about 1 carbon atom to about 10 carbon atoms.

Typically the epoxide may comprise any 1,2-alkyl epoxide in which the alkyl group is a linear hydrocarbon group of from about 6 to about 22 carbon atoms. Non-limiting examples of epoxides useful as reactant C in the practice of the present invention are: 1,2-epoxyoctane, 1,2-epoxytetradecane, 1,2-epoxyhexadecane, and 1,2-epoxyoctadecane.

Particularly useful as reactant C in the practice of the present invention are those epoxides or epoxide mixtures which are sold commercially under the tradename Vikolox® 14, 16, 18 and 20–24 and are available from Elf Atochem, or by Union Carbide under the trade name Cyracure® UVR 6216.

However, other epoxides containing heteroatoms or other functionality may be utilized as reactant C in accordance with the present invention such as glycidyl ethers and glycidyl esters. Particularly useful in the practice of the present invention would be those glycidyl esters or glycidyl ethers containing long chain or branched hydrocarbon groups. Exemplary but not limitive of these types of materials are glycidyl neodecanoate, glycidyl oleate, glycidyl octadecanoate, cresyl glycidyl ether, butyl glycidyl ether, hexyl glycidyl ether and dodecyl glycidyl ether.

Accordingly, the epoxide may be selected from the group consisting of 1,2-epoxyoctane, 1,2-epoxytetradecane, 1,2-epoxyhexadecane, 1,2-epoxyoctadecane, glycidyl neodecanoate, glycidyl oleate, glycidyl octadecanoate, cresyl glycidyl ether, butyl glycidyl ether, hexyl glycidyl ether, dodecyl glycidyl ether and mixtures of any of the foregoing.

Although it is preferable to carry out the first two steps of the process of the present invention in two separate steps, it is also recognized that the unsaturated diacid or corresponding anhydride (reactant B), diol (reactant A) and epoxide (reactant C) of the invention may be reacted in a single step. Accordingly, where the first two steps of the process of the present invention are carried out in separate steps, and wherein n>0, the process comprises the steps of: (a) reacting an unsaturated dicarboxylic acid or its corresponding anhydride with a diol to produce a first unsaturated polyester intermediate; (b) reacting said first unsaturated polyester intermediate with an epoxide to form a second intermediate unsaturated polyester having terminal beta-hydroxyalkylester groups; (c) reacting said second intermediate with a primary amine to form a third intermediate amine functional polyester having terminal beta-hydroxy ester groups; and (d) reacting said third intermediate amine functional polyester having terminal beta-hydroxy ester groups with an anhydride which is the same as or different from the anhydride of step (a) to provide an acylated amine functional polyester containing terminal beta-hydroxy ester groups product.

It is further important to note that in certain embodiments of the present invention it is contemplated to react the epoxide (reactant C) directly with a diacid or corresponding anhydride having an activated double bond (reactant B) with no diol (reactant A) present in order to obtain an intermediate of general structure III where n=0 and thus the additives of the present invention according to structure I where n=0. Thus, where n=0, a process for producing the additives of the present invention comprises the steps of: (a) reacting an unsaturated dicarboxylic acid with an epoxide to form a first intermediate unsaturated diester having terminal beta-hydroxyalkylester groups; (b) reacting said first intermediate unsaturated diester with a primary amine to form a second intermediate amine functional diester; and (c) reacting said second intermediate with an anhydride which is the same as or different from the anhydride of step (a) to provide an acylated amine functional diester containing terminal beta-hydroxy ester groups product.

In the third step of the process of the present invention, the second intermediate of general structure III is reacted with a primary amine (reactant D) to give a third intermediate of general structure IV as set forth in Equation (3) below.

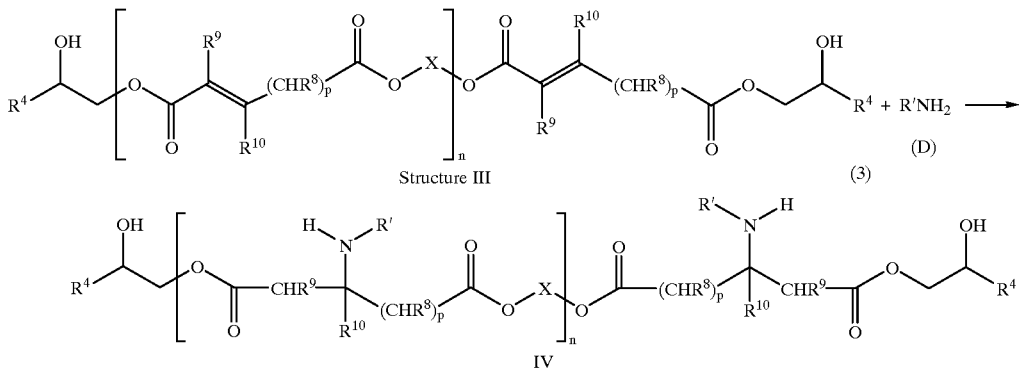

Structure III (3)

IV

The reaction of Equation (3) is typically conducted at a temperature of from about 25° C. to about 100° C. but is preferably carried out at a temperature of about 70° C. Primary amines useful in the practice of the present invention as reactant D are those of the general formula:

$$R'NH_2$$

where R' is a branched or linear, saturated or unsaturated hydrocarbon group of from about 6 carbon atoms to about 30 carbon atoms or an alkyloxypropyl or alkoxyethyl group wherein the alkyl group is a branched or linear saturated hydrocarbon group of from about 1 carbon atom to about 18 carbon atoms in length. Typically reactant D is a primary amine possessing a long chain alkyl group. Preferred amines for use as reactant D are those which contain a saturated or unsaturated hydrocarbon group of from about 8 to about 30 carbon atoms. Non-limiting examples of suitable long chain alkyl primary amines are n-hexylamine, octylamine, decylamine, dodecylamine, octadecylamine, iso-octadecylamine, oleyl amine, coco amine and tallow amine.

It is also contemplated that long chain alkyl amines containing heteroatoms such as nitrogen, sulfur and oxygen may be employed as reactant D in the practice of the present invention. Non-limiting examples of such amines are N-alkylethylenediamine such as N-hexylethylenediamine or N-dodecylethylenediamine; N-alkylpropanediamines such as N-tallow- 1,3-propanediamine, N-coco-1,3-propanediamine and N-oleyl-1,3-propanediamine or any combination of heteroatom containing amines.

Particularly useful as reactant D in the practice of the present invention are those primary amines containing an ether functional group. Non-limiting examples of such amines are: N-methoxypropylamine, N-hexyloxypropylamine, N-octyloxypropylamine, N-2-ethylhexyloxypropylamine, N-decyloxypropylamine, N-tridecyloxypropylamine, N-tetradecyloxypropylamine, N-hexadecyloxypropylamine, N-octadecyloxypropylamine or or mixture of any of the foregoing. Such ether amines are sold by Tomah Products under the names PA-10, PA-14, PA-1214, PA-16 and PA-17, PA-19 and PA-2220.

Also useful as reactant D in the practice of the present invention are those primary amines containing both oxygen and nitrogen as heteroatoms. Some non-limiting examples of such amines are: N-decyloxy-1,3-propanediamine, N-isodecyloxy-1,3-propanediamine, N-dodecyloxy-1,3-propanediamine, N-isododecyloxy-1,3-propanediamine, N-isotridecyloxy-1,3-propanediamine, N-tetradecyloxy-1,3-propanediamine or any combination of such amines. Primary amines containing both nitrogen and oxygen heteroatoms are sold by Tomah Products under the names DA-1214, DA-14, DA-16, DA-1618, DA-17 and DA-18.

Although not specifically mentioned above, other similar primary amines containing both nitrogen and oxygen heteroatoms may be envisioned as useful as reactant D in the practice of the present invention. Accordingly the amine reactant (D) may be selected from the group consisting of n-hexylamine, octylamine, decylamine, dodecylamine, octadecylamine, iso-octadecylamine, oleyl amine, coco amine, tallow amine, N-hexylethylenediamine, N-dodecylethylenediamine, N-tallow-1,3-propanediamine, N-coco-1,3-propanediamine, N-oleyl-1,3-propanediamine, N-methoxypropylamine, N-hexyloxypropylamine, N-2-ethylhexyloxypropylamine, N-decyloxypropylamine, N-tridecyloxypropylamine, N-tetradecyloxypropylamine, N-hexadecyloxypropylamine, N-octadecyloxypropylamine, N-decyloxy-1,3-propanediamine, N-isodecyloxy-1,3-propanediamine, N-dodecyloxy-1,3-propanediamine, N-isododecyloxy-1,3-propanediamine, N-isotridecyloxy-1,3-propanediamine, N-tetradecyloxy-1,3-propanediamine and mixtures of any of the foregoing.

In the final step of preparation of the additive compositions of matter of the present invention the third intermediate of general structure IV is reacted with a cyclic anhydride (reactant E) as set forth in Equation (4) below to produce the additive compositions of the present invention of general structure I.

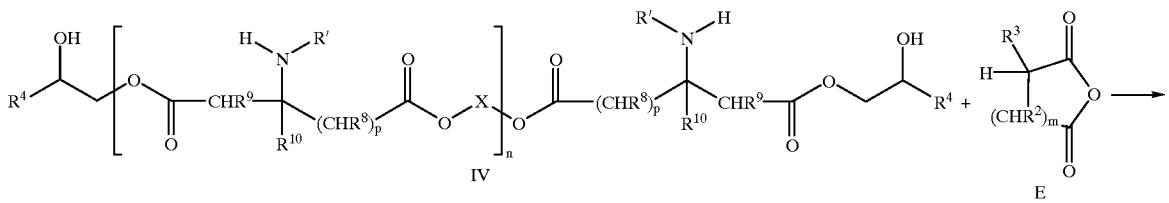

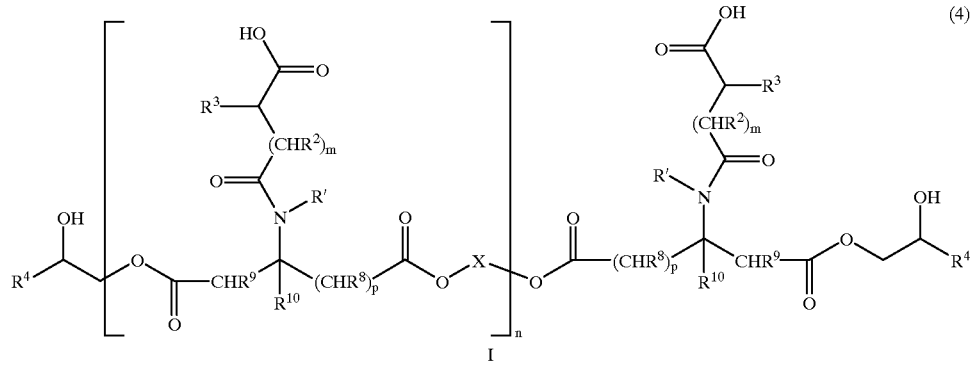

Cyclic anhydrides useful in the practice of the present invention as reactant E are typically those cyclic anhydrides of a linear diacid as set forth in the formula for reactant E above wherein $R^2$ and $R^3$ are independently the same or different groups selected from H or a saturated or mono-unsaturated, linear or branched hydrocarbon group of from about 12 to about 30 carbon atoms and m is an integer of from 1 to about 6. Exemplary but not limitive of such anhydrides are succinic anhydride and glutaric anhydride.

Also useful in the practice of the present invention as reactant E would be unsaturated cyclic anhydrides such as maleic anhydride, and accordingly, the reactant E may comprise the same anhydride as used as reactant B or a different anhydride. Accordingly the cyclic anhydride reactant (E) may be selected from the group consisting of succinic anhydride, glutaric anhydride, maleic anhydride and mixtures thereof. There are however restrictions as to substituents on the anhydride of reactant E. In general, those cyclic anhydrides containing bulky substituents such as long chain alkyl or alkenyl groups are not useful in the practice of the present invention and can detract from the activity of the composition of matter as a corrosion inhibitor for lubricants. Non-limiting examples of such anhydrides which are not useful in the practice of the present invention are dodecenylsuccinic anhydride, hexadecenylsuccinic anhydride, octadecenylsuccinic anhydride and iso-octadecenylsuccinic anhydride.

DESCRIPTION OF THE PREFERRED EMBODIMENTS

The following examples are intended to illustrate the present invention. They are not to be construed to limit the scope of the appended claims in any manner whatsoever.

EXAMPLE 1

A mono-functional carboxylic acid beta-hydroxy compound of the present invention is prepared by heating 58 parts of maleic acid with 240 parts of 1,2-epoxyhexadecane (available from Elf Atochem as Vikolox® 16) under a flow of nitrogen for about 6–7 hr or until the acid number of the reaction is less than 20 mg KOH/g. The temperature is decreased to 70° C. and 216 parts of 3-(decyloxy) propylamine (available from Tomah Products as PA-14) is slowly charged to the reaction at such a rate so as to maintain the temperature of the reaction. The mixture is heated for 2 hr and then 95 parts of succinic anhydride is added. The temperature is increased to 100° C. and the mixture is heated for 1 to 2 hr. A product in accordance with the present invention is obtained.

EXAMPLE 2

Repeating the procedure of Example 1, 58 parts of maleic acid is reacted with 268 parts of 1,2-epoxyoctadecane (available from Elf Atochem as Vikolox® 18), 216 parts of 3-(decyloxy)propylamine, and 95 parts of succinic anhydride. A product in accordance with the present invention is obtained.

EXAMPLE 3

Repeating the procedure of Example 1, 58 parts of maleic anhydride is reacted with 240 parts of 1,2-epoxyhexadecane (available from Union Carbide as UVR-6212), 256 parts of 3-(tridecyloxy)propylamine, and 95 parts of succinic anhydride. A composition in accordance with the present invention is obtained.

EXAMPLE 4

A dicarboxylic acid functional beta-hydroxyester compound of the present invention is prepared by first reacting 104 parts of neopentylglycol with 196 parts of maleic anhydride in the presence of about 1 part tridecylamine catalyst at 120° C. for about 1.5 to 2.0 hr. To the resulting intermediate is added 536 parts of 1,2-epoxyoctadecane (available from Elf Atochem as Vikolox 18) and the whole is heated at 150° C. for 5–6 hr or until the acid number drops below 15 mg KOH/g. The reaction mixture is cooled to 70° C. and 454 parts of 3-(decyloxy)propylamine (available from Tomah Products as PA-14) is added at such a rate so that the temperature of the reaction does not increase. The addition of the amine typically takes about 0.5 to 1.0 hr. To the reaction is added 200 parts of succinic anhydride and the whole is heated at 100° C. for 1 to 2 hr. A composition in accordance with the present invention is obtained.

EXAMPLE 5

Repeating the procedure of Example 4, 104 parts of neopentylglycol is reacted with 196 parts of maleic anhydride to give an intermediate diacid which is reacted with 480 parts of 1,2-epoxyhexadecane (available from Elf Atochme as Vikolox 16), followed by reaction with 454 parts of 3-(decyloxy)propylamine (available from Tomah Products as PA-14) and then 200 parts of succinic anhydride. A product in accordance with the present invention is obtained.

EXAMPLE 6

Repeating the procedure of Example 4, 104 parts of neopentylglycol is reacted with 196 parts of maleic anhydride to give an intermediate diacid which is reacted with 480 parts 1,2-epoxyoctadecane (available from Elf Atochem as Vikolox® 18), followed by reaction with 538 parts of 3-(tridecyloxy)propylamine (available from Tomah Products as PA-17) and then 200 parts of succinic anhydride. A composition in accordance with the present invention is obtained.

Anticorrosion Evaluations

The products of Examples 1–6, made in accordance with the process of the present invention, are evaluated for anti-corrosion properties using ASTM test D 665B, Procedure B (Standard Test Method for Rust-prevention Characteristics of Inhibited Mineral Oil in the Presence of Synthetic Sea Water) alone in several base oils, as well as in combination with other additives in model industrial formulations. In these tests, degreased polished steel spindles are stirred, fully immersed, at 60° C. in 300 mL of the lubricating composition. After 30 minutes, 30 mL of synthetic sea water is added. The spindles must be free of rust after 24 hr in order to pass the test. Although the test is officially only a pass/fail test, it is common for those typically running the test to qualitatively rate the failing spindles in order to compare the degree of rust protection in certain hard to inhibit formulations. A rating of #1–4 is used with #1 being a spindle with only a trace amount of rust (a near pass) and #4 being a spindle with severe rust covering the entire length. The general composition of the formulations used in the evaluations is given below:

Formulation 1: 500 ppm of the Example alone in a polyalpha olefin with a viscosity index of 121 and a kinematic viscosity of 100° C. of 4 cSt (Emery 3004).

Formulation 2: 500 ppm of the Example alone in a Group II ISO 46 severely hydrotreated base oil (Chevron RLOP).

Formulation 3: 1100 ppm of the Example along with 0.3% of a phenolic antioxidant, 0.11% of an alkylated diphenylamine antioxidant, 70 ppm of a triazole copper corrosion inhibitor, and 210 ppm of an amine phosphate antiwear additive in a Group II ISO 46 severely hydrotreated base oil (Chevron RLOP).

Formulation 4: 1100 ppm of the Example along with 0.3% of a phenolic antioxidant, 0.11% of an alkylated diphenylamine antioxidant, 70 ppm of a triazole copper corrosion inhibitor, 140 ppm of a corrosive mercaptothiadiazole antiwear additive and 210 of an amine phosphate antiwear additive in a Group II ISO 46 severely hydrotreated base oil (Chevron RLOP).

The results of the rust tests are given in Table 1 below—ASTM D 665B Rust Test Results.

For comparative purposes, a series of comparative examples are also prepared according to the following.

COMPARATIVE EXAMPLE A

The polyalphaolefin of Formulation 1 is evaluated in the ASTM D 665B Rust Test in the absence of any other additives.

COMPARATIVE EXAMPLE B

The Group II ISO VG 46 severely hydrotreated base oil of Formulation 2 is evaluated in the ASTM D 665B Rust Test in the absence of any other additives.

COMPARATIVE EXAMPLE C

Formulation 3 minus any of the inhibitors prepared in the Examples of the present invention is evaluated in the ASTM D 665B Rust Test in the absence of any other additives.

COMPARATIVE EXAMPLE D

Formulation 4 minus any of the inhibitors prepared in the Examples of the present invention is evaluated in the ASTM D 665B Rust Test in the absence of any other additives.

COMPARATIVE EXAMPLE E

A compound is made in accordance with Example 2 of U.S. Pat. No. 5,275,749. The product is incorporated into the Formulations 1–4 in place of the additive of the present invention and evaluated in the ASTM D 665B rust test.

COMPARATIVE EXAMPLE F

A monofunctional carboxylic acid long chain alkyl diester compound is prepared by heating a mixutre of 58 parts maleic acid with 192 parts of a mixture of $C_9$–$C_{11}$ alkyl alcohols (available from Shell Chemical as Neodol®) in the presence of tetrabutyl titanate at a temperature of about 160 to 180° C. with removal of the water of reaction for a period of about 6.5 hr or until the acid number of the reaction is <5.0 mg KOH per gram. The reaction is cooled to 70° C. and 204 parts of 3-(decyloxy)propylamine (available from Tomah Products as PA-14) is charged. The mixture is heated for 2 hr and then 90 parts of succinic anhydride is added. The temperature is increased to 100° C. and the mixture is heated for 1 to 2 hr.

The product is incorporated into the Formulations 1–4 in place of the additive of the present invention and evaluated in the ASTM D 665B rust test.

COMPARATIVE EXAMPLE G

A monofunctional carboxylic acid long chain linear alkyl diester is prepared in a two pot procedure by first heating a mixture of 40 parts maleic anhydride with 276 parts if a mixture of $C_{16}$–$C_{20}$ linear alkyl alcohols (available from Condea Vista as Alfol® 18) in the presence of 0.25 parts of tetrabutyl titanate at a temperature of about 160 to 180° C. with removal of the water of reaction for a period of about 6.5 hr or until the acid number of the reaction is <4.0 mg KOH per gram. The unreacted alcohol is distilled from the crude product at 220° C. at 2–3 mm Hg to give a di($C_{16}$–$C_{20}$ linear alkyl)maleate intermediate.

In a second step, to 100 parts of the di($C_{16}$–$C_{20}$ linear alkyl)maleate intermediate at 70° C. is charged slowly 43.4 parts of 3-(decyloxy)propylamine (available from Tomah Products as PA-14). The mixture is heated for 2 hr and then 19.1 parts of succinic anhydride is added. The temperature is increased to 100° C. and the mixture is heated for 1 to 2 hr.

The product is incorporated into the Formulations 1–4 in place of the additive of the present invention and evaluated in the ASTM D 665B rust test.

COMPARATIVE EXAMPLE H

A monofunctional carboxylic acid long chain branched alkyl diester compound is prepared in a two pot procedure by first heating a mixture of 40 parts maleic anhydride with 276 parts of a mixture of $C_{16}$–$C_{20}$ branched alkyl alcohols (available from Condea Vista as Alfol® E18) in the presence of 0.25 parts of tetrabutyl titanate at a temperature of about 160 to 180° C. with removal of the water of reaction for a period of about 6.5 hr or until the acid number of the reaction is <4.0 mg KOH per gram. The unreacted alcohol is distilled from the crude product at 220° C. at 2–3 mm Hg to give a di($C_{16}$–$C_{20}$ branched alkyl)maleate intermediate.

In a second step, to 100 parts of the di($C_{16}$–$C_{20}$ branched alkyl)maleate intermediate at 70° C. is charged slowly 43.4 parts of 3-(decyloxy)propylamine (available from Tomah Products as PA-14). The mixture is heated for 2 hr and then 19 parts of succinic anhydride is added. The temperature is increased to 100° C. and the mixture is heated for 1 to 2 hr.

The product is incorporated into the Formulations 1–4 in place of the additive of the present invention and evaluated in the ASTM D 665B rust test.

All of the test results for the Comparative Examples A–H are reported below in Table 1.

TABLE 1

ASTM D 665B RUST TEST RESULTS

| | Formulation 1 | Formulation 2 | Formulation 3 | Formulation 4 |
|---|---|---|---|---|
| Example 1 | Pass | Pass | Pass | Fail #1 |
| Example 2 | Pass | Fail #1 | Fail #1 | Pass |
| Example 3 | Pass | — | — | Fail #1 |
| Example 4 | Pass | Fail #1 | Pass | Pass |
| Example 5 | Pass | — | Pass | — |
| Comp. Example A | Fail #3 | — | — | — |
| Comp. Example B | — | Fail #3 | — | — |
| Comp. Example C | — | — | Fail #4 | — |
| Comp. Example D | — | — | — | Fail #4 |
| Comp. Example E | Fail #1 | Fail #3 | Fail #2 | Fail #3 |
| Comp. Example F | — | Fail #3 | Fail #3 | — |
| Comp. Example G | Fail #2 | Fail #4 | Fail #3 | Fail #3 |
| Comp. Example H | Fail #1 | Fail #1 | Fail #2 | Fail #2 |

From Table 1 above it can be seen that the examples in which additives of the present invention are employed perform significantly better than the comparative examples.

Many variations of the present invention will suggest themselves to those skilled in the art in light of the above-detailed description. All such obvious modifications are within the full intended scope of the appended claims.

All of the above-referenced patents, patent applications, publications and test methods are hereby incorporated by reference.

What is claimed is:

1. A composition of matter having the general structure (I)

(I)

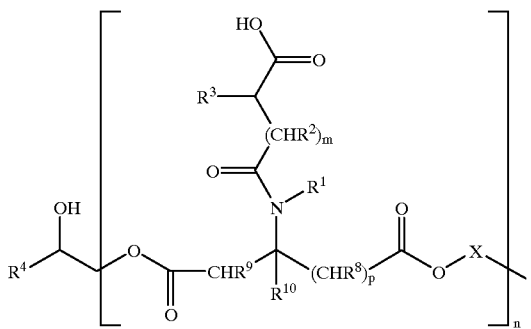

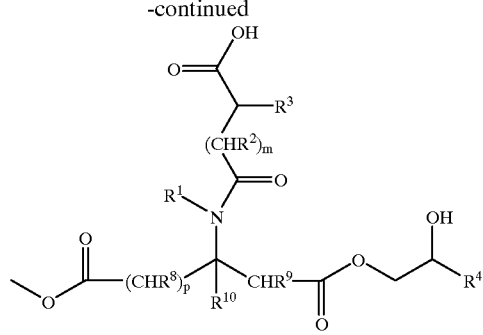

wherein
n is an integer of from 0 to about 5;
m is an integer of from 1 to about 6;
p is an integer of from 0 to about 6;
each X is independently the same or different saturated or unsaturated, branched or linear hydrocarbon diradical of from about 3 to about 8 carbon atoms, or an alkylene glycol or polyglycol of the general structure

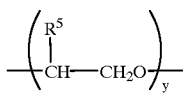

wherein $R^5$ is independently the same or different alkyl group of from 1 to about 4 carbon atoms or H and y is an integer from 1 to about 20;
each R' is independently the same or different branched or linear, saturated or unsaturated hydrocarbon group of from about 6 to about 30 carbon atoms or an alkyloxypropyl or alkoxyethyl group wherein the alkyl group is a branched or linear group of from about 1 to about 18 carbon atoms in length;
each $R^2$ and $R^3$ are independently the same or different saturated or mono-unsaturated, linear or branched hydrocarbon group of from about 12 to about 30 carbon atoms, or H; and
each $R^4$ is independently the same or different linear or branched saturated hydrocarbon group of from about 6 to about 22 carbon atoms; or a moiety of the formula

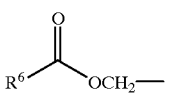

where each $R^6$ is a saturated or linear hydrocarbon group of from about 6 to about 20 carbon atoms; or a moiety of the formula

wherein $R^7$ is a hydrocarbon group of from 1 to about 10 carbon atoms; and
wherein each $R^8$, $R^9$ and $R^{10}$ independently comprises hydrogen or the same or different saturated or unsaturated, branched or linear, hydrocarbon radical having from 1 to about 20 carbon atoms.

2. A lubricating composition comprising a major proportion of an oil of lubricating viscosity and a minor proportion of from about 0.01 to about 10.0 percent by weight of the composition of matter as defined in claim 1.

3. A lubricating composition as defined in claim 2 wherein said oil comprises a poly-alpha-olefin.

4. A lubricating composition as defined in claim 2 wherein said oil comprises a Group II base oil.

5. A lubricating composition as defined in claim 2 wherein said oil comprises a Group III base oil.

6. A lubricating composition as defined in claim 2 wherein said composition further comprises a conventional additive selected from the group consisting of antiwear additives, antioxidants, yellow metal deactivators, viscosity index improvers, extreme pressure agents and mixtures of any of the foregoing.

7. A process for the preparation of a composition of matter as defined in claim 1, said process comprising:
   (a) reacting an unsaturated dicarboxylic acid or its corresponding anhydride with a diol, an epoxide or a combination thereof to form a first intermediate unsaturated polyester having terminal beta-hydroxyalkylester groups,
   (b) reacting said first intermediate unsaturated polyester with a primary amine to form a second intermediate amine functional polyester;
   (c) reacting said second intermediate with an anhydride which is the same as or different from the anhydride of step (a) to provide an acylated amine functional polyester containing terminal beta-hydroxy ester groups product.

8. A process as defined in claim 7 wherein said unsaturated diacid or corresponding anhydride comprises maleic anhydride or maleic acid.

9. A process as defined in claim 7 wherein said diol comprises neopentylglycol, ethylene glycol, methylpentanediol or a mixture of any of the foregoing.

10. A process as defined in claim 7 wherein said primary amine comprises octyloxypropylamine, decyloxypropylamine, tridecyloxypropylamine, dodecylamine or a mixture of any of the foregoing.

11. A process as defined in claim 7 wherein said anhydride is succinic anhydride or glutaric anhydride.

12. A process for producing a composition of matter as defined in claim 1 wherein n=0, said process comprising the steps of:
   (a) reacting an unsaturated dicarboxylic acid with an epoxide to form a first intermediate unsaturated diester having terminal beta-hydroxyalkylester groups;
   (b) reacting said first intermediate unsaturated polyester with a primary amine to form a second intermediate amine functional diester; and
   (c) reacting said second intermediate with an anhydride which is the same as or different from the anhydride of step (a) to provide an acylated amine functional polyester containing terminal beta-hydroxy ester groups product.

13. A process as defined in claim 12 wherein said unsaturated diacid or corresponding anhydride comprises maleic anhydride or maleic acid.

14. A process as defined in claim 12 wherein said primary amine comprises octyloxypropylamine, decyloxypropylamine, tridecyloxypropylamine, dodecylamine or a mixture of any of the foregoing.

15. A process as defined in claim 12 wherein said anhydride is succinic anhydride or glutaric anhydride.

16. A process for producing a composition of matter as defined in claim 1 wherein n>0, said process comprising the steps of:
   (a) reacting an unsaturated dicarboxylic acid or its corresponding anhydride with a diol to produce a first unsaturated polyester intermediate;
   (b) reacting said first unsaturated polyester intermediate with an epoxide to form a second intermediate unsaturated polyester having terminal beta-hydroxyalkylester groups;
   (c) reacting said second intermediate with a primary amine to form a third intermediate amine functional polyester having terminal beta-hydroxy ester groups; and
   (d) reacting said third intermediate amine functional polyester having terminal beta-hydroxy ester groups with an anhydride which is the same or different from the anhydride of step (a) to provide an acylated amine functional polyester containing terminal beta-hydroxy ester groups product.

17. A process as defined in claim 16 wherein said unsaturated diacid or corresponding anhydride of step (a) comprises maleic anhydride or maleic acid.

18. A process as defined in claim 16 wherein said diol comprises neopentylglycol, ethylene glycol, methylpentanediol or a mixture of any of the foregoing.

19. A process as defined in claim 16 wherein said primary amine comprises octyloxypropylamine, decyloxypropylamine, tridecyloxypropylamine, dodecylamine or a mixture of any of the foregoing.

20. A process as defined in claim 16 wherein said anhydride of step (d) comprises succinic anhydride or glutaric anhydride.

21. A process for producing a composition of matter having the general structure I:

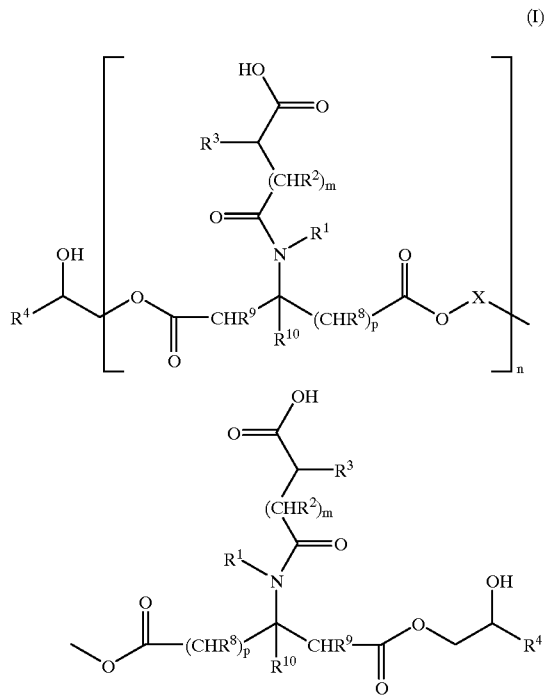

(I)

wherein
   n is an integer of from 0 to about 5;
   m is an integer of from 1 to about 6;
   p is an integer of from 0 to about 6;
   each X is independently the same or different saturated or unsaturated, branched or linear hydrocarbon diradical of from about 3 to about 8 carbon atoms, or an alkylene glycol or polyglycol of the general structure

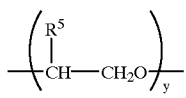

wherein $R^5$ is independently the same or different alkyl group of from 1 to about 4 carbon atoms or H and y is an integer from 1 to about 20;

each R' is independently the same or different branched or linear, saturated or unsaturated hydrocarbon group of from about 6 to about 30 carbon atoms or an alkyloxypropyl or alkoxyethyl group wherein the alkyl group is a branched or linear group of from about 1 to about 18 carbon atoms in length;

each $R^2$ and $R^3$ are independently the same or different saturated or mono-unsaturated, linear or branched hydrocarbon group of from about 12 to about 30 carbon atoms, or H; and each $R^4$ is independently the same or different linear or branched saturated hydrocarbon group of from about 6 to about 22 carbon atoms; or a moiety of the formula

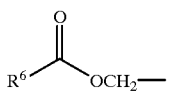

where each $R^6$ is a saturated or linear hydrocarbon group of from about 6 to about 20 carbon atoms; or a moiety of the formula

wherein $R^7$ is a hydrocarbon group of from 1 to about 10 carbon atoms; and each $R^8$, $R^9$ and $R^{10}$ independently comprises the same or different saturated or unsaturated branched or linear hydrocarbon radicals having from 1 to about 20 carbon atoms or H, said process comprising the steps of:
(a) reacting a diol of the general formula (A)

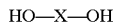 (A)

wherein X is as defined above with a cyclic anhydride of general formula (B) or its corresponding diacid (B)

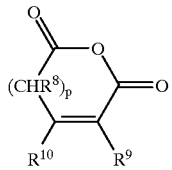

wherein p, $R^8$, $R^9$ and $R^1$ are as defined above to produce a first intermediate having the general formula:

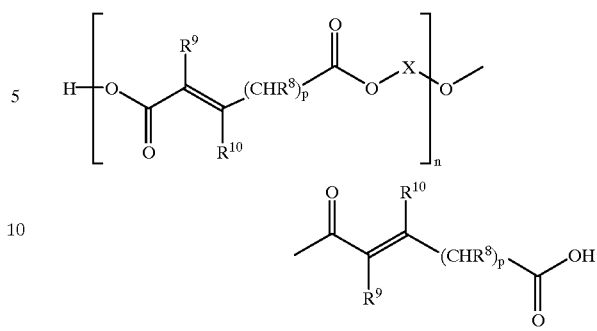

wherein X, n, p, $R^8$, $R^9$ and $R^{10}$ are as defined above;
(b) reacting said first intermediate with an epoxide having the general formula

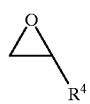

wherein $R^4$ is as defined above to produce a second intermediate having the general formula:

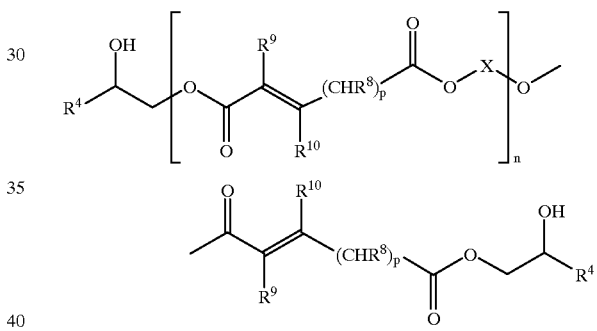

wherein $R^4$, p, X, n, $R^8$, $R^9$ and $R^{10}$ are as defined above;
(c) reacting said second intermediate with a primary amine of the general formula

R'NH$_2$ wherein R' is as defined above to produce a third intermediate having the general formula:

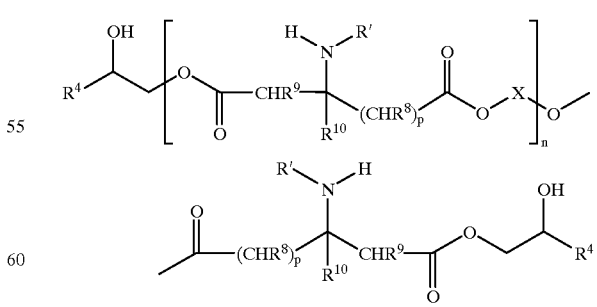

wherein $R^4$, $R^8$, $R^9$, $R^{10}$, p, X, n, and R' are as defined above and
(d) reacting said third intermediate with a cyclic anhydride of the general formula:

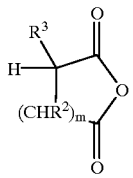

wherein $R^2$, $R^3$ and m are as defined above to produce the product of said general structure I.

22. A process as defined in claim 21 wherein said diol is selected from the group consisting of neopentyl glycol, ethylene glycol, propylene glycol, 1,4-butanediol, methylpentanediol, 1,6-hexanediol, ethylene diglycol, dipropylene glycol, polyethylene glycol, polypropylene glycol, 2,2-thiodiethanol, methyldiethanolamine and mixtures of any of the foregoing.

23. A process as defined in claim 21 wherein said dicarboxylic acid or its corresponding anhydride reactant B is selected from the group consisting of maleic acid, maleic anhydride, itaconic acid, itaconic anhydride and mixtures of any of the foregoing.

24. A process as defined in claim 21 wherein said epoxide is selected from the group consisting of 1,2-epoxyoctane, 1,2-epoxytetradecane, 1,2-epoxyhexadecane, 1,2-epoxyoctadecane, glycidyl neodecanoate, glycidyl oleate, glycidyl octadecanoate, cresyl glycidyl ether, butyl glycidyl ether, hexyl glycidyl ether, dodecyl glycidyl ether and mixtures of any of the foregoing.

25. A process as defined in claim 21 wherein said amine reactant is selected from the group consisting of n-hexylamine, octylamine, decylamine, dodecylamine, octadecylamine, iso-octadecylamine, oleyl amine, coco amine, tallow amine, N-hexylethylenediamine, N-dodecylethylenediamine, N-tallow-1,3-propanediamine, N-coco-1,3-propanediamine, N-oleyl-1,3-propanediamine, N-methoxypropylamine, N-hexyloxypropylamine, N-2-ethylhexyloxypropylamine, N-decyloxypropylamine, N-tridecyloxypropylamine, N-tetradecyloxypropylamine, N-hexadecyloxypropylamine, N-octadecyloxypropylamine, N-decyloxy-1,3-propanediamine, N-isodecyloxy-1,3-propanediamine, N-dodecyloxy-1,3-propanediamine, N-isododecyloxy-1,3-propanediamine, N-isotridecyloxy-1,3-propanediamine, N-tetradecyloxy-1,3-propanediamine and mixtures of any of the foregoing.

26. A process as defined in claim 21 wherein said cyclic anhydride reactant is selected from the group consisting of succinic anhydride, glutaric anhydride, maleic anhydride and mixtures thereof.

27. A process for producing a composition of matter having the general structure IA:

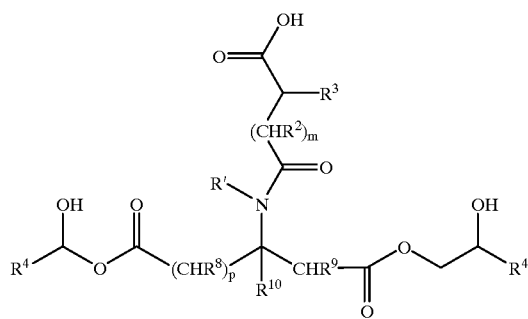

wherein m is an integer of from 1 to about 6;

p is an integer of from 0 to about 6;

each R' is branched or linear, saturated or unsaturated hydrocarbon group of from about 6 to about 30 carbon atoms or an alkyloxypropyl group wherein the alkyl group is a branched or linear group of from about 1 to about 18 carbon atoms in length;

each $R^2$ and $R^3$ are independently the same or different saturated or mono-unsaturated, linear or branched hydrocarbon group of from about 12 to about 30 carbon atoms, or H; and each $R^4$ is independently the same or different linear or branched saturated hydrocarbon group of from about 6 to about 22 carbon atoms; or a moiety of the formula where each $R^6$ is a branched or linear hydrocarbon group of from about 6 to about 20 carbon atoms; or a moiety of the formula

wherein $R^7$ is a hydrocarbon group of from 1 to about 10 carbon atoms; and each $R^8$, $R^9$ and $R^{10}$ independently comprises hydrogen or the same or different saturated or unsaturated, branched or linear, hydrocarbon radical having from 1 to about 20 carbon atoms, said process comprising the steps of:

(a) reacting a cyclic anhydride having the general formula (B)

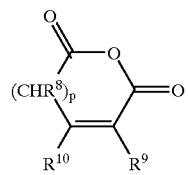

wherein p, $R^8$, $R^9$ and $R^{10}$ are as defined above, with an epoxide having the general formula

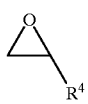

wherein $R^4$ is as defined above to produce a first intermediate having the general formula:

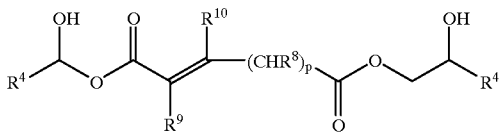

wherein p, $R^4$, $R^8$, $R^9$ and $R^{10}$ are as defined above;

(c) reacting said first intermediate with a primary amine reactant (D) of the general formula

R'NH$_2$ wherein R' is as defined above to produce a second intermediate having the general formula:

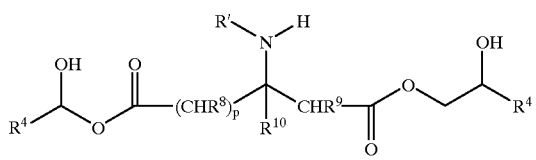

wherein $R^4$, $R^8$, $R^9$, $R^{10}$, p, and R' are as defined above and (d) reacting said second intermediate with a cyclic anhydride reactant (E) of the general formula:

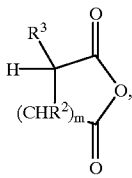 (E)

wherein $R^2$, $R^3$ and m are as defined above to produce the product of said general structure IA.

28. A process as defined in claim 27 wherein said dicarboxylic acid or its corresponding anhydride is selected from the group consisting of maleic acid, maleic anhydride, itaconic acid, itaconic anhydride and mixtures of any of the foregoing.

29. A process as defined in claim 27 wherein said epoxide is selected from the group consisting of 1,2-epoxyoctane, 1,2-epoxytetradecane, 1,2-epoxyhexadecane, 1,2-epoxyoctadecane, glycidyl neodecanoate, glycidyl oleate, glycidyl octadecanoate, cresyl glycidyl ether, butyl glycidyl ether, hexyl glycidyl ether, dodecyl glycidyl ether and mixtures of any of the foregoing.

30. A process as defined in claim 27 wherein said primary amine reactant (D) is selected from the group consisting of n-hexylamine, octylamine, decylamine, dodecylamine, octadecylamine, iso-octadecylamine, oleyl amine, coco amine, tallow amine, N-hexylethylenediamine, N-dodecylethylenediamine, N-tallow-1,3-propanediamine, N-coco-1,3-propanediamine, N-oleyl-1,3-propanediamine, N-methoxypropylamine, N-hexyloxypropylamine, N-2-ethylhexyloxypropylamine, N-decyloxypropylamine, N-tridecyloxypropylamine, N-tetradecyloxypropylamine, N-hexadecyloxypropylamine, N-octadecyloxypropylamine, N-decyloxy-1,3-propanediamine, N-isodecyloxy-1,3-propanediamine, N-dodecyloxy-1,3-propanediamine, N-isododecyloxy-1,3-propanediamine, N-isotridecyloxy-1,3-propanediamine, N-tetradecyloxy-1,3-propanediamine and mixtures of any of the foregoing.

31. A process as defined in claim 27 wherein said cyclic anhydride reactant (E) is selected from the group consisting of succinic anhydride, glutaric anhydride, maleic anhydride and mixtures thereof.

* * * * *